United States Patent

Kahn

(10) Patent No.: US 6,906,200 B2
(45) Date of Patent: Jun. 14, 2005

(54) PRODUCTION OF N-VINYL PYRROLIDONE

(75) Inventor: Andrew P. Kahn, Eagleville, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 268 days.

(21) Appl. No.: 10/261,357

(22) Filed: Oct. 1, 2002

(65) Prior Publication Data

US 2004/0063970 A1 Apr. 1, 2004

(51) Int. Cl.$^7$ .................... C07D 207/267; C07D 207/26
(52) U.S. Cl. ................ 548/552; 548/543; 548/551
(58) Field of Search .................. 548/543, 551, 548/552

(56) References Cited

U.S. PATENT DOCUMENTS

| 2,669,570 A | | 2/1954 | Schnizer ................ 260/326.5 |
| 3,821,245 A | * | 6/1974 | Kanetaka et al. ............ 548/552 |
| 5,569,770 A | * | 10/1996 | Kuo et al. .................. 548/543 |

* cited by examiner

*Primary Examiner*—Joseph K. McKane
*Assistant Examiner*—Janet L. Coppins
(74) *Attorney, Agent, or Firm*—William C. Long

(57) ABSTRACT

N-vinyl pyrrolidone is produced by dehydration of N-hydroxyethyl pyrrolidone in the presence of an amorphous mixed oxide catalyst such as an amorphous Ca/Zn oxide catalyst.

3 Claims, No Drawings

PRODUCTION OF N-VINYL PYRROLIDONE

BACKGROUND OF THE INVENTION

1. Field of the Invention

The present invention relates to the production of N-vinyl pyrrolidone by the catalytic dehydration of N-hydroxyethyl pyrrolidone using an amorphous mixture of metal oxides such as a mixture of calcium and zinc oxides.

2. Description of the Prior Art

It is known to produce N-vinyl pyrrolidone by the catalytic dehydration of N-hydroxyethyl pyrrolidone. U.S. Pat. No. 2,669,570 describes this reaction and suggests that suitable catalysts for the reaction include calcium oxide, aluminum oxide as well as mixtures of aluminum oxide-iron oxide-potassium hydroxide.

U.S. Pat. No. 3,821,245 also describes the reaction and suggests as catalyst an oxide of zirconium, thorium, cerium, zinc and chromium or a mixture of these oxides. The oxide catalysts are sintered at 500–1200° C. prior to use. In Example 14 a zinc oxide catalyst baked at 700° C. for 2 hours is used while in Example 17 a mixture of zinc oxide and chromium oxide also baked at 700° C. for 2 hours was used.

U.S. Pat. No. 5,569,770 shows the reaction using a mixed oxide of Group IV elements or an oxide of Group IV elements modified by Group I or Group II elements. High temperature calcination of the catalyst is taught.

BRIEF DESCRIPTION OF THE INVENTION

In accordance with the present invention, N-vinyl pyrrolidone is produced by dehydration of N-hydroxyethyl pyrrolidone using an amorphous mixed metal oxide such as Ca/Zn oxide or Mg/Zn oxide as catalyst.

DETAILED DESCRIPTION

In carrying out the process of the present invention, the reaction conditions which are employed for dehydration of N-hydroxyethyl pyrrolidone are generally the same as those taught, for example in U.S. Pat. No. 5,569,770 the disclosure of which is incorporated herein by reference. Reaction temperatures of about 250–500° C., preferably 300–450° C. are suitable. Atmospheric pressure is suitable but higher or lower pressures can be used.

It is important in practice of the invention that the mixed oxide catalyst be amorphous, and to achieve this, the mixed oxides are not treated at temperatures sufficiently high to cause significant crystal formation. The XRD pattern seen for fresh Ca/Zn oxide catalyst (30 wt. % Ca) catalyst is fairly broad, with the most dominant phase observed arising from $CaCO_3$. After the fresh catalyst is calcined to 500° C., the x-ray pattern of crystalline ZnO emerges. Samples that have been calcined >700° C. all show the same pattern, that of crystalline ZnO and CaO. Where the catalyst shows the presence of substantial crystalline components the utility of the catalyst in the N-hydroxyethyl pyrrolidone dehydration to N-vinyl pyrrolidone is markedly inferior.

It is preferred that the catalyst not be subjected to temperatures in excess of 450° C., preferably not in excess of 400° C. for best results. Commercially available metal oxides are dried during preparation at lower or moderate temperatures and thus are amorphous rather than crystalline. The amorphous metal oxides are suitably used in the invention.

The mixed oxide catalysts used herein consist essentially of ZnO in admixture with one or more of CaO, SrO and MgO. The Zn content expressed as the element ranges from about 35–75 wt. % based on the total weight of the mixed metal oxides.

The following examples illustrate the invention; unless otherwise indicated the metal oxides used were conventional, commercially available materials.

EXAMPLE 1

A tube (0.81" ID with 0.185" thermowell) was packed with 10 cc (10.95 g) of Ca/Zn oxide (30 wt. % Ca) that had been ground to 14/30 mesh. The tube was heated in an electric furnace to 348° C. under a nitrogen flow of 18 SLH (standard liters per hour). N-hydroxyethyl pyrrolidone was fed at 9.9 g/h to the top of the reactor and the product was recovered in an ice trap for analysis. After 1 hour, N-vinyl pyrrolidone was obtained in 82.0% yield (97.8% conversion of N-hydroxyethyl pyrrolidone with 83.9% selectivity to N-vinyl pyrrolidone).

COMPARATIVE EXAMPLE 1

Example 1 is repeated except the Ca/Zn oxide is calcined in air to 500° C. prior to running. Analysis by XRD shows the presence of a crystalline ZnO phase. After 1 hour at 366° C., N-vinyl pyrrolidone was obtained in 44.0% yield (62.0% conversion of N-hydroxyethyl pyrrolidone with 70.9% selectivity to N-vinyl pyrrolidone).

COMPARATIVE EXAMPLE 2

Example 1 is repeated except the Ca/Zn oxide is calcined in air to 700° C. prior to use. Analysis by XRD shows the presence of both crystalline ZnO and CaO phases. After 1 hour at 359° C., NVP was obtained in 11.5% yield (76.1% conversion of N-hydroxyethyl pyrrolidone with 15.1% selectivity to N-vinyl pyrrolidone).

COMPARATIVE EXAMPLE 3

Example 1 is repeated except $CaCO_3$ (6.07 g, 14×30 mesh) is used. After 1 hour at 377° C., N-vinyl pyrrolidone was obtained in 2.7% yield (19.7% conversion of N-hydroxyethyl pyrrolidone with 13.6% selectivity to N-vinyl pyrrolidone).

The above examples demonstrate the superior results achieved through practice of the invention (Example 1) as compared to similar examples where the mixed oxide is calcined at 500° C. (Comparative Example 1), at 700° C. (Comparative Example 2), and where only a calcium carbonate catalyst is used (Comparative Example 3).

Examples 2–4 show that the Ca content can vary and still produce a desirable result:

EXAMPLE 2

Example 1 is repeated except Ca/Zn oxide (8.85 g, 14×30 mesh, 9 wt. % Ca) is used. After 1 hour at 336° C., N-vinyl pyrrolidone was obtained in 69.8% yield (99.9% conversion of N-hydroxyethyl pyrrolidone with 69.8% selectivity to N-vinyl pyrrolidone).

EXAMPLE 3

Example 1 is repeated except Ca/Zn oxide (8.63 g, 14×30 mesh, 16 wt. % Ca) is used. After 1 hour at 331° C., N-vinyl pyrrolidone was obtained in 67.5% yield (84.8% conversion of N-hydroxyethyl pyrrolidone with 79.6% selectivity to N-vinyl pyrrolidone).

EXAMPLE 4

Example 1 is repeated except Ca/Zn oxide (9.30 g, 14×30 mesh, 16 wt. % Ca) is used. After 1 hour at 359° C., N-vinyl pyrrolidone was obtained in 80.4% yield (94.8% conversion of N-hydroxyethyl pyrrolidone with 84.8% selectivity to N-vinyl pyrrolidone).

The following examples show practice of the invention using an amorphous Mg/Zn mixed oxide:

EXAMPLE 5

Example 1 is repeated except Mg/Zn oxide (7.15 g, 14×30 mesh, 20 wt. % Mg) is used. After 4 hours at 356° C., N-vinyl pyrrolidone was obtained in 66.7% yield (99.4% conversion of N-hydroxyethyl pyrrolidone with 67.1% selectivity to N-vinyl pyrrolidone).

EXAMPLE 6

Example 1 is repeated except Mg/Zn oxide (6.79 g, 14×30 mesh, 10 wt. % Mg) is used. After 2 hours at 360° C., N-vinyl pyrrolidone was obtained in 88.3% yield (98.9% conversion of N-hydroxyethyl pyrrolidone with 89.3% selectivity to N-vinyl pyrrolidone).

COMPARATIVE EXAMPLE 4

Example 1 is repeated except MgO (7.93 g, 14×30 mesh) is used. After 1 hour at 368° C., N-vinyl pyrrolidone was obtained in 26.6% yield (63.8% conversion of N-hydroxyethyl pyrrolidone with 41.7% selectivity to N-vinyl pyrrolidone).

The above results demonstrate the improved N-vinyl pyrrolidone production using amorphous Mg/Zn oxide catalyst (Examples 5 and 6) as compared to use of only MgO catalyst (Comparative Example 4).

I claim:

1. The process for the production of N-vinyl pyrrolidone which comprises dehydrating, N-hydroxyethyl pyrrolidone in the presence of an amorphous mixed oxide catalyst consisting essentially of ZnO in admixture with one or more of CaO, SrO, and MgO, the Zn content of the catalyst expressed as the element being about 35–75 wt % based an the weight of mixed oxides.

2. The process of claim 1 wherein the catalyst is amorphous mixed Ca/Zn oxide.

3. The process of claim 1 wherein the catalyst is an amorphous mixed Mg/Zn oxide.

* * * * *